United States Patent [19]
Craik et al.

[11] Patent Number: 5,747,322
[45] Date of Patent: May 5, 1998

[54] RECOMBINANT CRAB COLLAGENASE

[75] Inventors: Charles S. Craik, San Francisco, Calif.; Christopher A. Tsu, Boulder, Colo.

[73] Assignee: The Regents of the University of California, Oakland, Calif.

[21] Appl. No.: 650,129

[22] Filed: May 9, 1996

[51] Int. Cl.$^6$ .............. C12N 9/64; C12N 9/48; C12N 9/50
[52] U.S. Cl. .............. 435/226; 435/212; 435/219; 530/857
[58] Field of Search .............. 435/212, 219, 435/226; 530/857

[56] References Cited

U.S. PATENT DOCUMENTS

| | | | |
|---|---|---|---|
| 5,143,837 | 9/1992 | Sova et al. | 435/212 |
| 5,418,157 | 5/1995 | Lin et al. | 435/220 |

OTHER PUBLICATIONS

Corey et al., "Trypsin Specificity Increased Through Substrate-Assisted Catalysis," Biochemistry, 34, pp. 11521–11527 (1995).

Grant et al., "Amino Acid Sequence of a Collagenolytic Protease Hepatopancreas from the Fiddler Crab, Uca pugilator," Biochemistry, 19, pp. 4653–4659 (1980).

Tsu et al., "The Substrate Specificity of Uca pugilator Collagenolytic Serine Protease 1 Correlates with the Bovine Type I Collagen cleavage Sites," J. Biol. Chem., 269:30, pp. 19565–19572 (1994).

Willett et al., "Engineered Metal Regulation of Trypsin Specificity," Biochemistry, 34, pp. 2172–2180 (1995).

Eisen et al. (1973) Biochemistry 12, 1814–1822.

*Primary Examiner*—Rebecca E. Prouty
*Assistant Examiner*—Elizabeth Slobodyansley
*Attorney, Agent, or Firm*—Majestic, Parsons, Siebert & Hsue

[57] ABSTRACT

An isolated sequence is provided that encodes crab procollagenase (Seq ID NO 5) that upon cleaving off the 29 amino acid propeptide (Seq ID NO 6) transforms into an active collagenase (Seq ID NO 4). The procollagenase has the MW of about 26.6 kD and the mature collagenase has a MW of 23.5 kD. Procollagenase mutated at positions 201 and 235 is also provided. A storage-stabilized composition providing long-term, shelf-stable protease that can be readily activated when collagenolytic activity is desired is disclosed.

11 Claims, 3 Drawing Sheets

FIG. 1A

```
   1  GAATTCCGGAAAATATCCAAAAACAATTGCAGTAAAAAAAAAAATCAGGTTGGGCGTGTTG    60
  61  GTTTTACAACTGAGAAGCAGCATTTTCTGTGTTAAACCCTATTCTTTAAGTAATAGCAAG   120
 121  ACAAATTTTTCCATTTATCCTACATGATCGTCAAGCTTGCTCTCATCCTCGTCTGCGTCG   180
 181  CCCTAGCTAGCGGCAACCCCGCGGCTGGCACAGAATGGCGTTGGAAGTCTCCGAAGCCAC   240
 241  TTATGACACCCATTGGCCCTGTAAAGTCATCCCGCATTGTGGGTGGCGTTGAGGCAGTGC   300
 301  CCAACTCGTGGCCCCACCAGGCAGCTCTCTTCATTGACGACATGTACTTCTGCGGTGGCT   360
 361  CCCTCATATCCCCTGAGTGGATCCTGACTGCTGCTCACTGCATGGATGGGGCCGGTTTTG   420
 421  TGGATGTGGTTCTGGGGGCTCACAATATTCGTGAGGACGAAGCCACACAGGTAACCATAC   480
 481  AGAGCACCGACTTCACGGTCCACGAGAACTATAACTCTTTCGTCATATCGAATGATATCG   540
 541  CCGTCATCAGGCTGCCTTCACCAGTAACCCTGACTGCGGCAATTGCTACCGTTGGTCTGC   600
 601  CTTCAACTGATGTCGGTGTTGGAACGGTAGTAACTCCAACTGGCTGGGGCCTACCATCAG   660
 661  ACTCTGCCCTTGGGATTTCTGACGTTCTTCGCCAAGTGGATGTCCCCATCATGAGTAATG   720
 721  CAGACTGTGACGCAGTCTACGGCATTGTGACAGATGGAAATATCTGCATTGACTCAACTG   780
 781  GTGGCAAGGGTACTTGTAACGGTGACTCAGGTGGCCCTCTCAACTATAACGGACTGACCT   840
 841  ATGGCATCACTTCCTTCGGTGCGGCGGCTGGTTGTGAGGCTGGCTACCCAGATGCCTTCA   900
 901  CTCGCGTCACTTATTTCCTGGACTGGATCCAGACACAGACGGGCATCACTCCATAAGCGA   960
 961  CAAGGACAAGATACGACTGATGGGAGCCCCAAAGATTGTATATGTGTCTTAATGGACACT  1020
1021  GCCCTCAGTATCAAGGCTTCAACTGAAGAATGATTTCTTTCAGTTTTATATGAATAAATC  1080
1081  CATACAGAAGCATAAAAAAACCGGAATTC  1109
```

RECOMBINANT CRAB COLLAGENASE

This invention was made with Government support under Grant No. MCB 9219806, awarded by the National Science Foundation. The Government has certain rights in this invention.

FIELD OF THE INVENTION

The present invention generally relates to collagenolytic proteases, and more particularly to expression systems including a recombinant crab collagenase gene for expressing crab procollagenase in a stabilized form that when activated is useful for proteolytic applications.

BACKGROUND OF THE INVENTION

Collagen is the most abundant protein found in vertebrates and serves as a structural protein of tissues. The several types of collagen are a family of genetically related proteins that exhibit fundamentally similar secondary and tertiary protein structures. Type I Collagen is the most prevalent and is found, for example, in skin, tendon and bone.

Collagenolytic serine protease 1 (EC 2.4.21.32) isolated from the hepatopancreas of the fiddler crab, *Uca pugilator*, is the first known serine protease capable of cleaving native type I triple helical collagen. Serine collagenases have since been isolated from a variety of organisms, and are thought to be primarily involved in the digestion of foodstuffs. In addition to its eponymous activity, crab collagenase also possesses significant trypsin, chymotrypsin, and elastase-like substrate specificities, and is the most efficient serine protease known in the hydrolysis of P1-Gln and P1-Leu amide substrates. Preferences in the cleavage of peptide bonds within a relaxed domain of collagen mirrors the enzymes' specificity toward small peptidyl substrates. The ability of collagenase, but not trypsin, chymotrypsin or other homologs, to cleave triple helical collagen arises from unique extended substrate binding sites in collagenase.

In 1980 an amino acid sequence was published that was said to be of fiddler crab collagenase (Grant, et al. *Biochemistry*, 19 pp. 4653–4659). The postulated amino acid sequence of fiddler crab collagenase identified it as a member of the chymotrypsin-like serine proteases. However, as will be described hereinafter, this published amino acid sequence was incorrect.

U.S. Pat. No. 5,143,837, inventors Sova et al., issued Sep. 1, 1992, describes an enzyme complex derived from crabs. This complex is said to be useful to cleave standard synthetic and protein substrates and to possess a chymotrypsin trypsin and elastase-like activity; however, complexes such as the complex described by Sova et al., have variable properties, particularly from batch to batch. That is, such complexes may include multiple forms of collagenase, and contaminating non-collagenase proteases. Such variability complicates efforts to use the desired collagenase. This tends to be particularly frustrating for researchers and to persons involved in tissue culture, where batch to batch variations can, at best, create difficulties for use. Thus, a reliably pure, homogenous collagenase would be desirable.

U.S. Pat. No. 5,418,157, issued May 23, 1995, inventors Lin et al., describe genetically engineered *E. coli* said to carry vectors containing inserts that code for Clostridium histolyticum collagenase, having a molecular weight of about 68,000 Daltons. However, this collagenase is considerably larger than crab collagenase and is also far less specific. The collagenase described by Patent '157 is less specific than fiddler crab collagenase due to its evolution as a non-specific enzyme serving a nutritive role for the soil bacterium that produces it. Thus, the bacterial collagenase degrades any protein material with which it comes into contact. Its degradation results in amino acids and the organism follows the resulting amino acid gradient produced for nutritive purposes. Collagen is just one of many proteins that the bacterial collagenase degrades, and so it does so in a very non-specific fashion.

BRIEF DESCRIPTION OF THE DRAWINGS

FIG. 1A sets out the DNA sequence encoding recombinant collagenase of this invention with underlining illustrating different sequence portions;

FIG. 1B is the amino acid sequence (with underlining illustrating an optional part of the sequence) of the cloned collagenase.

SUMMARY OF THE INVENTION

Figure 2A:
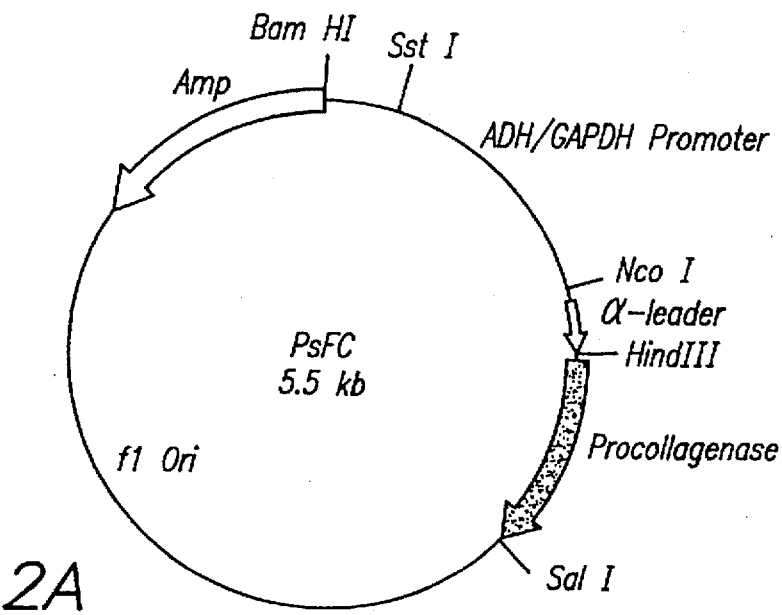
FIGS. 2A and 2B show a construction of two plasmids used in expressing recombinant collagenase in yeast.

In one aspect of the present invention a DNA sequence is provided that encodes crab serine collagenase I. The sequence coding for the mature collagenase may also include a sequence that directs protein folding (hereinafter sometimes the "zymogen" form, or procollagenase). The procollagenase when expressed from the inventive DNA sequence has a molecular mass of 26,619 daltons while the mature, recombinant collagenase has a molecular mass of 23,500 daltons. Both proteins may be expressed in a variety of expression systems. Manipulations of the collagenase gene and expression systems are also provided by this invention, such as to engineer collagenase variants.

For example, two variants of crab collagenase I were prepared, which demonstrate use of mutagenesis at the S1 site of collagenase in order to engineer specificity. Thus, crab collagenase I was engineered to remove Asp226 (chymotrypogen numbering) from the S1 site and to substitute Gly (crab collagenase D226G), which resulted in an enzyme that preferentially binds hydrophobic residues at P1. Crab collagenase D226G retains more than 50% of wild-type $k_{cat}/K_m$ versus peptidyl P1 hydrophobic substrates (Phe, Leu, Met, Ala) but maintains only 1–5% of $k_{cat}/K_m$ versus cognate positively charged substrates (Arg, Lys, Orn). Moreover, there is a three fold reduction in the $k_{cat}/K_m$ value towards P1-Gln. In essence, the normally broad specificity of crab collagenase I was significantly narrowed by removing the negative charge from the S1 site, and the resulting variant, crab collagenase D226G, thus represents a more specific protease than the wild type enzyme. Restoration of the S1 negative charge by substituting Gly189 with Asp (crab collagenase D226/ G/G189D) led to recovery of 40–70% of wild type $k_{cat}/K_m$ value versus positively charged substrates, while maintaining 15–40% of wild type $k_{cat}/K_m$ versus hydrophobic substrates. This variant favors P1-Arg over P1-Lys by approximately 40 fold, nearly double he discrimination between Arg and Lys of the wild type enzyme.

The recombinant fiddler crab collagenase provided by this invention is advantageous over other collagenases, such as bacterial collagenase, in that fiddler crab collagenase has evolved to be quite specific for collagen since collagen is a major food source for the crab. Fiddler crab collagenase degrades collagen in a specific fashion. Producing collagenase in a recombinant version in accordance with this invention provides more pure and homogenous collagenase and permits the ready production of reagent quantities and qualities. Since the gene for collagenase is now available through the invention, one has the ability to manipulate the encoded protein. Thus, the invention provides site-specific protease variants as well as a reliable source of obtaining homogenous collagenase with excellent specificity. Contaminants as may otherwise be present with endogenous collagenase are avoided. Further, the present invention permits production of isolatable recombinant fiddler crab collagenase in zymogen form from expression systems such as yeast, bacteria or insect cells. Because the zymogen form is more storage stable, but the "PRO" sequence can be readily clipped from the collagenase molecule when activity is desired, more reliably shelf stable products for various applications are also provided through practice of the present invention.

DESCRIPTION OF THE PREFERRED EMBODIMENTS

Recombinant Collagenase and Procollagenase

Figure 1B:
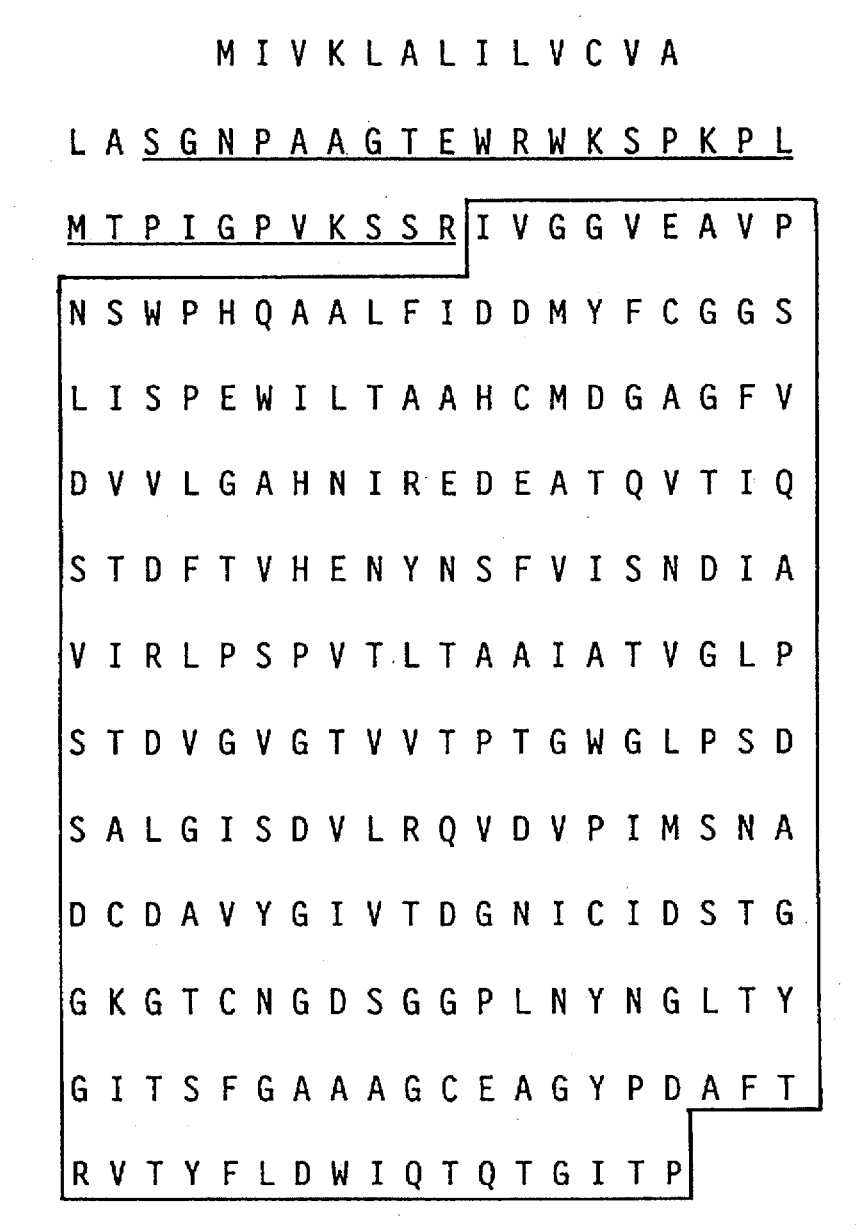

We have cloned, expressed, and characterized crab serine collagenase 1. An isolated DNA sequence encoding this collagenase is set out by FIG. 1A.

The codon ATT within the box of FIG. 1A is for isoleucine, which is the first amino acid of the mature collagenase. The boxed codon AGC upstream of boxed ATT of FIG. 1A begins the sequence (underlined) which together with that of the mature collagenase constitutes the zymogen form. In the zymogen form the collagenase folds correctly and also is maintained in an inactive, or off state. Boxed TAA downstream of boxed ATT of FIG. 1A is the stop codon for collagenase expression. Thus, Sequence I.D. No:1 (SEQ ID NO:1) is the sequence for the mature collagenase, while Sequence I.D. No:2 (SEQ ID NO:2) sets out the zymogen form of the coding sequence. Sequence I.D. No: 3 (SEQ ID NO:3), which includes the dashed underlined portion upstream of boxed AGC, further includes a "pre-sequence" useful for secretion of the enzyme in yeast. This pre-sequence will change, depending upon the expression system chosen. As illustrated by FIG. 1A, the pre-sequence is that of the fiddler crab, used by it for secretion. In yeast, one typically would use the α-factor leader sequence, in bacteria there are many choices, one of which is the STII leader sequence, and in baculovirus the gp67 leader sequence. (However, in bacteria, secretion can pose difficulties.)

Turning to FIG. 1B, the mature form of the cloned collagenase (illustrated in the boxed section) has 226 amino acid residues, a molecular mass of 23,500 daltons, and has the amino acid sequence as illustrated and set out by Sequence I.D. No:4 (SEQ ID NO:4). Sequence I.D. No: 5 (SEQ ID NO:5) is the zymogen form, where the underlined upstream 29 amino acid residues of FIG. 1B constitute the "off switch" for the protease. These 29 amino acid residues themselves are useful as a switch for proteases and are Sequence I.D. No:6. (SEQ ID NO:6)

In a preferred embodiment for practising the invention, a storage-stabilized composition is provided that is useful for collagen degragation applications. A storage-stabilized composition includes a first component in which a protein that is capable of cleaving collagen when in active form is in the presence of sufficient amounts of an acidic agent to at least retard, and preferably reversibly eliminate, the activity of collagen cleavage. However, the protein of the first component may be selectively placed into active form (that is, the inactivity is reversed) by neutralization of the acidic agent. This may be accomplished by use of a second component that includes a basic agent. The second component may optionally also include an activating enzyme. When the second component is admixed with the first component, then neutralization occurs so as to return the protein to its active form in which condition it is ready for applications in which collagen degregation are desired.

The first and second components together may constitute a kit. For example, the first and second components can be maintained as liquids in an apparatus which maintains the two liquids separately until delivery. The apparatus can include one compartment for the first component and another compartment for the second component.

Procollagenase as previously described, when in the presence of an acidic agent so as to place a formulation below approximately pH 4, more preferably, about pH 2, is thus in inactive form. The procollagenase is thereby substantially storage-stabilized until activity is desired. Suitable acidic agents include the well known and conventional inorganic and organic acids. When these acids are neutralized by conventional basic agents, then the recombinant pocollagenase will auto-activate; however, if desired to speed the activation process, a small (catalytic) quantity of activating enzyme can be added. For example, trypsin cleaves the peptide bond between arginine and isoleucine. Therefore, with reference to Sequence I.D. No:2, either by auto-activation at neutral pH or by the addition of small (catalytic) amounts of activating enzyme, the "PRO" sequence will be removed (at the junction of the arginine and isoleucine) and the resulting recombinant collagenase be placed in active form.

The pure and isolated protein from a recombinant expression system of the invention provides extremely specific collagenolytic activity. Thus, the collagenase expressed from the DNA sequence of Sequence I.D. No:1 cleaves collagen at peptide bonds at the carboxyl termini of arginine, leucine and glutamine residues.

Expression of the Collagenase Gene

The recombinant collagenase of the invention is synthesized in host cells transformed with vectors containing DNA encoding the collagenase. Preferred host cells are yeast, bacterial and baculoviral cells. "Transformation" of host cells means introducing DNA into an organism so that the DNA is replicable, either as an extrachromosomal element or by chromosomal integration. A vector is a replicable nucleic acid construct. An expression vector for the invention is a replicable DNA construct in which a DNA sequence encoding collagenase (or a collagenase variant) is operatively linked to suitable control sequences capable of effecting the expression of collagenase (or a collagenase variant) in a suitable host. Such control sequences include a transcriptional promoter, an optional operator sequence to control transcription, a sequence encoding suitable mRNA ribosomal binding sites, and sequences which control termination of transcription and translation.

DNA regions are operatively linked when they are functionally related to each other. For example, DNA for a pre-sequence or secretory leader is operatively linked to DNA for a polypeptide if it is expressed as a pre-protein which participates in the secretion of the polypeptide. A promoter is operatively linked to a coding sequence if it controls the transcription of the sequence or a ribosome binding site is operatively linked to a coding sequence if it is positioned so as to permit translation. Generally, operatively linked means contiguous and, in the case of secretory leaders, contiguous and in reading phase.

Preferred prokaryotic vectors include plasmids such as those capable of replication in *E. coli* (such as, for example, pBR322, ColE1, pSC101, PACYC 184, φVX. Such plasmids are, for example, disclosed by Maniatis et al. (*Molecular Cloning, A Laboratory Manual*, Cold Spring Harbor, NY (1982)) now updated by Sambrook et al. (2nd Ed. 1990). Bacillus plasmids include pC194, pC221, pT127, etc. Such plasmids are disclosed by Gryczan (The *Molecular Biology of the Bacilli*, Academic Press, NY (1982), pp. 307–329). Suitable Streptomyces plasmids include pIJ101 (Kendall et al., J. Bacteriol., 169:4177–4183 (1987)), and Streptomyces bacteriophages such as φ2C31 (Chater et al., *Sixth International Symposium on Actinomycetales Biology*, Akademiai Kaido, Budapest, Hungary (1986), pp. 45–54). Pseudomonas plasmids are reviewed by John et al. (*Rev. Infect. Dis.*, 8:693–704 (1986)), and Izaki (*JPN. J. Bacteriol.*, 33:729–742 (1978)).

Preferred eukaryotic plasmids include BPV, vaccinia, SV40, 2-micron circle, etc., or their derivatives. Such plasmids are well known in the art (Botstein et al., *Miami Wntr. Symp.*, 19:265–274 (1982); Broach, *The Molecular Biology of the Yeast Saccharomyces: Life Cycle and Inheritance*, Cold Spring Harbor, N.Y., pp. 445–470 (1981); Broach, *Cell*, 28:203–204 (1982); Bollon et al., *J. Clin. Hematol. Oncol.*, 10:39–48 (1980); Maniatis, *Cell Biology: A Comprehensive Treatise*, Vol. 3, Gene Expression, Academic Press, NY, pp. 563–608 (1980)).

Once the vector or DNA sequence containing the construct has been prepared for expression, the DNA construct may be introduced into an appropriate host cell by any of a variety of suitable means: transformation, transfection, conjugation, protoplast fusion, electroporation, calcium phosphate-precipitation, direct microinjection, etc. After the introduction of the vector, recipient cells are grown in a selective medium, which selects for the growth of vector-containing cells. Expression of the cloned gene sequence results in the production of the collagenase. This can take place in the transformed cells as such, or following the induction of these cells to differentiate (for example, by administration of bromodeoxyuracil to neuroblastoma cells or the like). The expressed protein may be isolated and purified in accordance with conventional conditions, such as extraction, precipitation, chromatography, affinity chromatogrphy, electrophoresis, or the like.

Among prokaryotic hosts suitable for use in carrying out the present invention are strains of the bacteria *E. coli* although Bacillus and other general are also useful. Techniques for transforming these hosts, and for expressing foreign DNA sequences cloned in them, are well known in the art (see, for example, Sambrook et al., eds., *Molecular Cloning: A Laboratory Manual*, Cold Spring Harbor Laboratory, Cold Spring Harbor, N.Y., 2nd Ed. 1989). Vectors used for expressing foreign DNA in bacterial hosts will generally contain a selectable marker, such as a gene for antibiotic resistance, and a promoter which functions in the host cell. Appropriate promoters include the trp (Nichols and Yanofsky, *Meth. in Enzymology* 101:155, 1983), lac (Casadaban et al., *J. Bact.* 143:971–980, 1980), TAC (Russell et al., *Gene* 20:231–243, 1982), and phage lambda promoter systems. Plasmids useful for transforming bacteria include pBR322 (Bolivar et al., Gene 2:95–113, 1977), the pUC plasmids (*Messing, Meth. in Enzymology* 101:20–77, 1983; and Vieira and Messing, *Gene* 19:259–268, 1982), PCQV 2 (Queen, J. Mol. Appl. Genet. 2:1–10, 1983), and derivatives thereof.

Eukaryotic microorganisms, such as the yeast *Saccharomyces cerevisiae*, or filamentous fungi including Aspergillus species, may also be used as host cells. We tend to prefer expression in a yeast system. Techniques for transforming yeast are described, for example, by Beggs (Nature 275:104–108, 1978). Aspergillus species may be transformed according to known procedures, for example, that of Yelton et al. (Proc. Natl. Acad. Sci. USA 81:1740–1747, 1984). Expression vectors for use in yeast include YRp7 (Struhl et al., Proc. Natl. Acad. Sci. USA 76:1035–1039, 1979), YEp13 (Broach et al., *Gene* 8:121–133, 1979), pJDB248 and pJDB219 (Beggs, ibid.), and derivatives thereof. Such vectors will generally comprise a selectable marker, such as the nutritional marker TRP1, which allows selection in a host strain carrying a trp1 mutation, or the POT1 selectable marker, which permits selection in a tpi- strain grown in rich medium (Kawasaki and Bell, EP 171, 142). Preferred promoters for use in yeast expression vectors include promoters from yeast glycolytic genes (Hitzeman et al., *J. Biol. Chem.* 255:12073–12080, 1980; Alber and Kawasaki, *J. Mol. Appl. Genet.* 1:419–434, 1982; Kawasaki, U.S. Pat No. 4,599,311) or alcohol dehydrogenase genes (Young et al., in *Genetic Engineering of Microorganisms for Chemicals*, Hollaender et al., eds., p. 335, Plenum, N.Y., 1982; and Ammerer, *Meth. in Enzymology* 101:192–201, 1983).

Various baculoviruses, including those that infect cotton bollworm, *Helicoverpa zea*, tobacco budworm, *Heliothis virescens*, Douglas fir tussock moth, orgia pseudotsugata, gypsy moth, *Lymantria dispar*, alfalfa looper, *Autographa californica*, European pine fly, *Neodiiprion sertifer*, and coddling moth, *Laspeyresia pomonella*, are useful in practice of this invention. For example *Autographa californica* nuclear polyhedrosis virus (ACNPV) may be constructed as a recombinant baculovirus and various transfer vectors of ACNPV are available for expression of foreign genes in agricultural pest insects including *Spodoptera exignia, Spodoptera fungiporda, Heliothis zea, Heliothis armigen, Heliothis virescens, Trichoplusia ni*, and related insects. Miller, *Ann. Rev. Microbiol.*, 42:177–199 (1988). Some of these vectors can be used for insertion of foreign genes without disrupting the original polyhedrin gene. Recombinant AcNPVs produced by these transfer vectors will produce polyhedral inclusion bodies as well as foreign gene products. Recombinant viruses having polyhedral inclusion bodies are especially preferred for their ability to infect an insect orally, which is the natural mode of infection of insects in the field. Among the transfer vectors which can be used for expression of foreign genes in AcNPV is pAcUW (B), Weyer et al., *J. Gen. Virol.*, 71:1525–1534 (1990). The pAcUW(B) transfer vector contains the original polyhedrin gene with the original promoter and an insertion site (BgIII) for expression of the foreign genes after the p10 promoter.

Preparation of Collagenase Variants

The crab serine collagenase I gene is useful as a starting point, or precursor, for engineering modifications to yield one or more protease variants.

The catalytic triad of collagenase contains an aspartate, a histidine, and a serine. The active-site histidine acts as a general base to accept the proton from serine, allowing nucleophilic attack and subsequent hydrolysis of a peptide bond. Removal of the active-site histidine will destroy the normal activity of the enzyme. Thus, substrate-assisted catalysis requires the bound substrate to provide the histidine necessary for general base catalysis and peptide bond hydrolysis.

By combining the strategy of substrate-assisted catalysis with S1 mutagenesis, specific three residue recognition sites can be engineered. For example, an engineered collagenase variant specific for cleavage between X and Arg or Lys in the sequence -His-X-Arg/Lys- can be made through crab collagenase H57A. In this example, His is the P2 residue, X represents either aromatic, aliphatic, basic or acid residues depending on the specific collagenase S1 mutants, and Arg/Lys is P1'. Thus, variants of the invention can have the improved properties of specific P1 preferences for aliphatic amino acids, for aromatic amino acids, for basic amino acids, for acidic amino acids, or of having a specific P2 preference for histidine by changing the histidine at position 57 to alanine, glycine or serine. By removing the catalytic histidine from the enzyme the amino acid must now come from the substrate, providing specificity for the P2 position.

Sequence and structural similarities between trypsin, chymotrypsin, and elastase have suggested a classical model in which only a few critical residues in the P1 pocket (S1 site) determine substrate specificity. However, mutagenesis experiments have shown that S1 residues are not the sole determining factor of specificity. Because crab serine collagenase I already possesses subsites that accommodate a myriad of substrates, modulating specific substrate specificities through protein engineering to favor, for example, aromatic residues or basic residues, has now become feasible with the collagenase gene provided herein.

Therefore, in addition to preparation of recombinant crab collagenase and of expression systems including recombinant genes of the invention, other aspects of the invention are the use of a recombinant expression system for fiddler crab serine I collagenase in making variants of fiddler crab serine I collagenase with engineered specificities.

For example, the aspartic acid residue at 226 has been modified to glycine by site-directed mutagenesis since removal or relocation of the negatively charged group results in a variant enzyme retaining very high activities towards selected substrates. Restoration of the negative charge in another collagenase variant D226G/G189D regenerates nearly full activity toward basic substrates while introducing a five-fold decrease in $k_{cat}/K_m$ toward hydrophobic amino acids. Thus, by virtue of having a recombinant collagenase gene provided through the subject invention, the primary binding site of the collagenase can be readily modified for specificity (in distinction to the extensive mutagenesis required to alter specificity in trypsin).

Uses of the Recombinant Crab Collagenase Gene and Expressed Collagenase

The purified collagenase produced by genetically engineered recombinant expression systems as described can be used for any application in which it is desired to digest collagen.

Collagenases are useful as reagents in pharmaceutical applications and can also assist in purification and truncation of collagen at a unique site. Collagenase itself has plastic surgery applications, such as enzymatic debridement. For example, particular applications include digesting connective tissues and releasing embedded cells without destroying cell membrane and other essential structures.

The unique site for collagen is the ¾, ¼ site. Collagen is around 1000 amino acids long and is formed by three strands intertwining to form a triple helix. True collagenases cleave collagen at around 750 amino acids to produce a ¾ and a ¼ fragment (crab collagenase does this at a site slightly different than mammalian collagenases. Clostridium histolyticum does not provide such cleavage, as it is just a nonspecific protease that degrades collagen, but not specifically).

Collagenases are also useful as laundry detergent additives, since protein stains are sensitive to collagenolytic activity.

More generally, proteases are valuable tools for the manipulation, e.g. cleavage and semi-synthesis of amide and ester bonds of proteins and peptides. However, in comparison to the stringent specificities of restriction endonucleases, most proteases lack selectivity for unique primary sequences. Highly selective proteases do exist which possess the ability to cleave proteins at unique sites, but their collective specificities are few, the discrimination against closely related sequences is poor, and the proteases are generally not available in reagent quantities. As a result, there are applications for which no adequate protease is available.

Engineered proteases from variants of the recombinant collagenase gene, which possess a high degree of specificity, therefore have a number of applications to which they may be put. For example, such new proteases with altered specificities could supplement existing proteases in the mapping of proteins, much as restriction endonucleases are used for the mapping of nucleic acids. Modified proteases could also be used to cleave folded proteins at naturally occurring cleavage sites to generate desired truncated products or to isolate protein domains. Alternatively, recombinant fusion proteins could be cleaved at engineered sites to liberate the desired native protein.

In summary, aspects of the invention include purified and isolated DNA sequences which encode collagenase so as to obtain substantially pure crab collagenase, expression vectors containing such DNA sequences, expression systems that can be formed by introducing the collagenase DNA containing vector into a suitable host, and manipulated DNA segments having a region encoding collagenase variants, such as variants with a selected P1 preference.

These aspects of the invention are illustrated by the following several examples. Example 1 illustrates the detection and isolation of DNA for crab collagenase and the expression of recombinant crab procollagenase through a yeast expression system. Example 1 further characterizes the expressed recombinant collagenase, and sets out some studies concerning catalytic efficiency. Example 2 describes the production of some site-directed variants of collagenase, including several at the S1 site and another at the S1' site. Example 3 describes the use of another expression system (bacterial) for expressing recombinant procollagenase in insoluble form (later converted to soluble form). Example 4 describes preparation of cloning a recombinant collagenase without the need for zymogen activation. Example 5 describes use of a baculovirus expression system. These examples are intended to illustrate, but not to limit, the present invention.

EXAMPLE 1

RNA Isolation and CDNA Library Construction.

Live fiddler crabs (*Uca pugilator*) were obtained from Gulf Specimen Marine Laboratory (Panacea, Fla.). The hepatopancreas was dissected, immediately frozen in liquid nitrogen and stored at −80° C. Total RNA was extracted from the frozen hepatopancreas using guanidine thiocyanate and partially purified by ultracentra-fugation through a cesium trifluoroacetate gradient. Poly-A$^+$ RNA was isolated from total RNA by hybridization to biotinylated oligo dT, which was recovered from solution using streptavidin coated paramagnetic beads (Poly-ATract, Promega). All RNA was stored under ethanol at −80° C.

A Lambda Zap II crab hepatopancreas cDNA library was constructed and amplified by Clontech Laboratories (Palo Alto, Calif.). The library contains $1.8 \times 10^6$ independent clones, with a CDNA insert size range of 1.0 to 5 kb.

Isolation of the Crab Collagenase cDNA

The polymerase chain reaction (PCR) was used to amplify a fragment of the crab collagenase cDNA from the Uca pugilator hepatopancreas library. Two degenerate PCR primers denoted FCN1 and FCC1 were synthesized based on the amino and carboxy termini of the mature protease amino acid sequence. FCN1, sometimes hereinafter SEQ. ID NO:7 is: 5'-TGCTCTAGA-GTI-GA(A/G)-GCI-GTICCI-AA(T/C)-TCI-TGG-3'. FCC1, sometimes hereinafter SEQ ID NO:8 is: 5'-GATAAGCTTGA-TTA-IGG-IGT-IAT-ICC-IGT (T/C)TG-IGT-(T/C)TG-IGT-CCA-3'. Inosine was used to reduce the degeneracy of the oligo pool by broadening the base-pairing potential at these positions. Five μl of library stock containing $3.5 \times 10^8$ phage were subjected to PCR with the FCN1 and FCC1 oligos using standard conditions. The PCR reaction consisted of 5 cycles of 1 min annealing at 44° C., 2 min polymerization at 72° C. and 1 min denaturation at 95° C.; followed by 30 cycles with an elevated annealing temperature of 50° C. The single-band PCR product was purified by agarose gel electrophoresis and Geneclean (Bio 101). The PCR product was sequenced by the dideoxy method, using Sequenase T7 DNA polymerase (US Biochemical) and the FCN1 and FCC1 primers.

The library was plated with *E. coli* strain XL1-Blue, adsorbed in duplicate to nitrocellulose filters, denatured and fixed according to standard manufacturer's instructions (Stratagene, Clontech). The probe 5'-CA-(G/A)AA-(G/A)TA-CAT(G/A)TC-(G/A)TC-(G/A/T)AT-(G/A)AA-3, SEQ. I.D. No:9 was a degenerate oligodeoxynucleotide based on the FIDDMYFC (residues 34–42) motif of the crab collagenase protein sequence. The 5' end of the degenerate probe was radiolabelled using T4 polynucleotide kinase and $[\gamma^{-32}p]$ ATP (New England Biolabs) and hybridized to the plaque lifts overnight at 42° C. The filters were washed at 47° C. and autoradiographed. Excision and rescue of the bluescript plasmid containing the cDNA insert was carried out according to the manufacturer's instructions (stratagene). Both strands of the cDNA clones comprising the composite map were sequenced by the dideoxy method using Sequenase.

Subsequent screens of the library were carried out using homologous probes generated by $[\alpha^{-32}P]$ dCTP (New England Nuclear) PCR from the collagenase clone denoted FC1. Either an EcoRI fragment containing the entire FC1 cDNA or a 200 bp EcoRI-NheI fragment of the 5' end of the cDNA were used as templates. Under the conditions of limiting dCTP and high template concentration, the reaction products resembled those of primer extension rather than fragment amplification. These homologous probes were hybridized overnight at 50° C. The filters were then washed at 65° C. and autoradiographed.

Detection and Isolation of Crab Collagenase Clones from the Hepatopancreas CDNA Library Crab collagenase clones were detected in the cDNA library by two methods utilizing degenerate oligonucleotides based on the amino acid sequence of the protease. In the first method, a set of oligonucleotides, FCN1 and FCC1, complementary to the amino and carboxy termini of mature collagenase were used in the polymerase chain reaction to amplify a DNA fragment from the cDNA library. A single, intense band of approximately the size of the mature protease (670 bp) was produced. Direct sequencing of the PCR DNA yielded sequence around His57, Gly1189 and Phe215 (chymotrypsinogen numbering) of the collagenase. The lambda cDNA library was also screened with a degenerate oligonucleotide complementary to the FIDDMYFC sequence of the collagenase (residues 34–42). This sequence was chosen for three reasons: (1) minimal sequence identity to other serine proteases; (2) proximity to the 5' end of the gene permitting isolation of more full-length clones from the oligo dT primed cDNA library; and (3) low amino acid coding degeneracy (96-fold degenerate). 40,000 plaques were screened, yielding 10 primary, 7 secondary and 3 tertiary isolates.

The most complete clone, denoted FC1, contains a 15 amino acid signal sequence, a 29 amino acid zymogen peptide, and the entire 226 amino acid mature form of the collagenase, as well as 143 bases of 5' and 153 bases of 3' untranslated sequence (see FIG. 1A, SEQ. ID NO:1). The likely start codon of clone FC1 is a non-optimal AGG (Arg), rather than the expected ATG (Met). Further screening of the library was indicated, as no ATG start codon could be located in any reading frame near the expected start site. Screening of an additional 30,000 plaques with PCR fragments generated from the FC1 template yielded 15 primary, 9 secondary and 6 tertiary isolates. Two clones, FC2 and FC3, yielded necessary sequence data. Clone FC2 provided the requisite ATG start codon, though uncharacterized recombination events rendered the 5' untranslated region and the 3' third of the CDNA unusable. Clone FC3 encoded the complete collagenase zymogen minus the signal sequence and 5' untranslated region, while the 3' untranslated region extends into the poly A tail. The CDNA presented in FIG. 1A is a composite of FC1, the ATG start of FC2 and the poly-A tail of FC3. The coding sequences of all clones were identical.

Amino Acid Alignment and Secondary Structure Modelling of Crab Collagenase

The putative signal peptide of crab collagenase was determined by the hydrophobic nature of the amino acids. The amino acid sequences of crab procollagenase and shrimp chymotrypsinogen (EMBL accession number X66415), rat anionic trypsinogen 2 (PIR, TRRT2; PDB, 1BRA), bovine chymotrypsinogen A (PIR, KYBOA; PDBOA; 7GCH) and porcine proelastase 1 (PIR, ELPG; PDB, 3EST) were aligned using the PILEUP program of the GCG software package (Genetics Computer Group, Madison, Wisconsin), and consensus structural constraints, as derived from alignment of proteases of known three-dimensional structure.

Figure 2B:
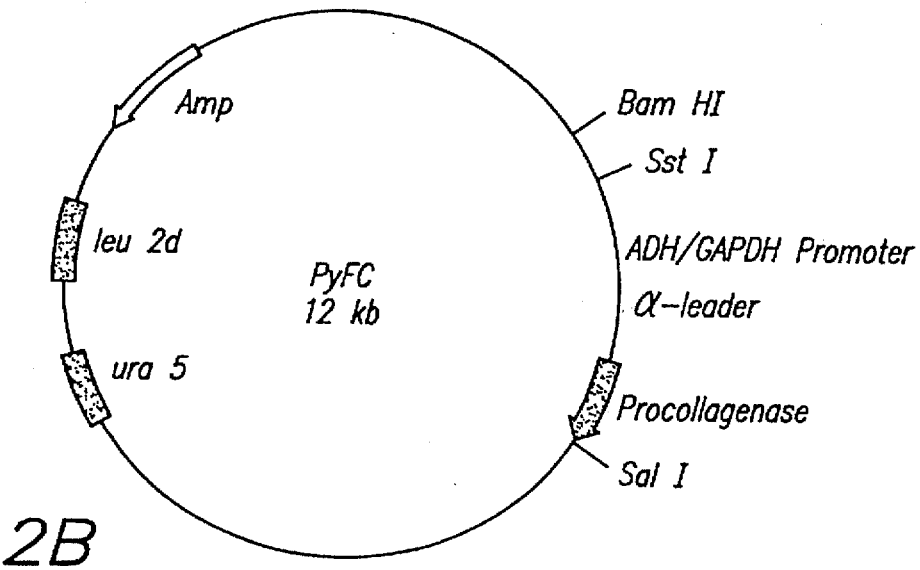

Preparation for the Expression and Purification of the Recombinant Crab Procollagenase The zymogen form of crab collagenase (procollagenase) was cloned in frame with the α-factor leader of the PSFC vector. PCR with Pfu DNA polymerase (Stratagene) was used to generate the necessary Hind III and Sal I restriction endonuclease cleavage sites. This construct was named PsFC, which is illustrated by FIG. 2A. The full expression vector was created by subcloning the PsFC Sst I/Sal I fragment containing the ADH/GAPDH promoter, Co-factor leader and procollagenase into the PyFC 1 μM circle yeast/E. coli shuttle vector, yielding PyFC, which is illustrated by FIG. 2B.

The PyFC construct was electroporated into the AB110 or DM10lα strain of *S. cerevisiae* and transformants were selected by growth at 30° C. on SD (8% glucose) plates lacking uracil or leucine. A small culture was grown up in SD-Leu⁻x (8% glucose) for 36 hours at 30° C. with gentle shaking. This culture was diluted 1:20 into YPD (2% glucose) and grown for 60–72 hours at 30° C. with gentle shaking. The yeast cells were removed by centrifugation and the supernatant was adjusted to pH 7.4 by addition of Tris base to a final concentration of 10 mM. DEAE chromatography was performed as described for the enzyme isolated from the crab hepatopancreas. Fractions were assayed for procollagenase either by western blot analysis or by activation with trypsin. The activation assay contained 20 μl of sample, 5 μl of 1 μM TPCK-treated bovine trypsin (Sigma) and 200 μl of 400 μM Suc-AAP-Leu pNA in 50 mM Tris, 100 mM NaCl, 20 mM $CaCl_2$, pH 8.0. The reaction course was monitored at 405 nM at room temperature using a UVmax microtitre plate reader (Molecular Devices). The fractions containing procollagenase were pooled and adjusted to 50 mM Tris, 100 mM NaCl, 20 mM $CaCl_2$, pH 8.0. Addition of a 0.5% volume of TPCK-treated, agarose immobilized bovine trypsin (Sigma) resulted in complete activation of the zymogen after 2 hours of gentle shaking at room temperature, as monitored by increase in activity towards Suc-AAP-Leu-pNA. The activated collagenase was further purified by BPTI affinity chromatography. An overall yield of 1 mg recombinant collagenase per liter of yeast culture was achieved.

Kinetic Analysis of Recombinant Collagenase, Trypsin, Chymotrypsin and Elastase Recombinant rat trypsin was purified by published techniques. Other reagents were purchased from the following sources: TLCK treated bovine chymotrypsin (Sigma), porcine elastase (Calbiochem), bovine calf skin collagen (US Biochemical), Suc-AAPAbu-pNA (Bachem of California) and Z-GPR-Sbzl (Enzyme Systems Products). All other substrates were from Bachem Bioscience. All enzyme active site titrations, substrate calibrations, kinetic assays and collagen digestions were carried out by conventional methods. Briefly, pNA kinetic assays were monitored at 410 nm ($E_{410}$=8,480 $M^{-1}$ $cm^{-1}$) in 50 mM Tris, 100 mM NaCl, 20 mM $CaCl_2$, pH 8.0 at 25° C. 1 to 4% DMF or 2% $Me_2SO$ was present in the final reaction buffer. Benzylthioester kinetic assays were monitored at 324 nm ($E_{324}$=19,800 $M^{-1}cm^{-1}$) in the above buffer at 25° C. with the inclusion of 250 μM dithiodipyridine (Chemical Dynamics) and 2% DMF. AMC spectrofluorimetric assays were monitored at an excitation wavelength of 380 nm and an emission wavelength of 460 nm, under conditions identical to those for pNA. Assays were done in duplicate for 5 substrate concentrations, except for Suc-AAP-Asp-pNA, for which the $kcat/K_m$ was determined using 3 substrate concentrations in duplicate. The steady state kinetic parameters were determined by nonlinear regression fit to the Michaelis Menten equation. Standard deviation in $k_{cat}/K_m$ was generally less than 10%, though individual rate and binding constants varied to a greater extent. In particular, error for elastase was 15% in $k_{cat}$ versus Suc-AAP-Val-pNA and 25% in $K_m$ versus Suc-AAP-Ile-pNA. Kinetic parameters were plotted versus P1 residue volume and the hydrophobicity constant, π.

Sequence Analysis of Recombinant Collagenase. The previously published amino acid sequence of fiddler crab collagenase (Grant, supra) contained six different amino acid residues relative to the sequence predicted from the cDNA. These six changes appear to reflect errors in the original amino acid sequence determination, rather than amino acid variation due to the cloning of an isozyme of crab collagenase. The discrepancies and the possible causes are: I106V, carryover of Val 105; S110v weak detection of Ser; S164N/N165S, acid induced N→O acyl shift, weak detection of Ser and Asn; N192D and N202D, acid induced deamination (chymotrypsinogen numbering, where the first letter denotes the amino acid predicted from the cDNA sequence and the second letter denotes the amino acid from the original sequence determination). One of the errors in the protein sequence, N192D, maps to the rim of the S1 site, and must be considered regarding the possible effect of the negative charge on substrate recognition. The other errors appear to map to the surface of the enzyme.

The amino acid sequence of mature crab collagenase is homologous to the mammalian serine proteases trypsin, chymotrypsin and elastase (35% identity), and shrimp chymotrypsin (75% identity), another serine collagenase. Virtually all major structural features of a chymotrypsin-like serine protease are found in crab collagenase. Three disulfide bonds (residues 42:58, 168:182 and 191:220) are conserved. Conservation of the double β barrel core is strict, and the surface loops are similar in size to those of the vertebrate paradigms. Some are of unique sequence and may play a role in determining the broad substrate specificity of crab collagenase. An unusual crab collagenase active site geometry of Gly189 and Asp226, as compared to Asp189 and Gly226 in trypsin, is maintained in the CDNA.

Comparison of the zymogen peptides of these enzymes serves to further delineate the group, as they are of variable length and share little identity. Crab collagenase and shrimp chymotrypsin possess zymogen peptides which are 2 to 3 times longer than those of the vertebrate proteases. The purpose of these large activation domains is unclear, as they are not required for heterologous expression of vertebrate proteases such as trypsin. The activation site of procollagenase, VKSSR-IVGG, is more similar to those of chymotrypsinogen, SGLSR-IVVG, and proelastase, ETNAR-VVGG, which are activated by trypsin, than that of trypsinogen DDDDK-IVGG, which is activated by enterokinase. Crab collagenase may self activate or another trypsin-like protease in the crab hepatopancreas may perform this function. The primary sequence alignment suggests that crab collagenase and shrimp chymotrypsin are members of a novel serine protease subfamily.

Expression and Purification of Crab Collagenase in S. Cerevisiae

Crab procollagenase was cloned into the PYFC S. cerevisiae expression vector as a fusion with the α-factor signal sequence under the transcriptional control of the ADH/GAPDH promoter and ADH terminator, yielding the PyFC construct. Yeast containing PyFC secrete a 30 kDa protein into the media which cross-reacts with anti-crab collagenase antibodies on western blots.

The recombinant procollagenase is purified from the yeast media in much the same manner as the native collagenase from crab hepatopancreas. DEAE chromatography, followed by trypsin activation and subsequent BPTI affinity chromatography are used to purify the recombinant enzyme to homogeneity.

Activity of Recombinant Collagenase Versus Type I Collagen

The collagenolytic activity of the recombinant collagenase was compared directly to that of the endogenous enzyme isolated from the crab hepatopancreas. The specificity and rate of collagen cleavage are similar. The signature ¾ and ¼-length fragments are identical in morphology, including the ¼-length triplet. Furthermore, the collagenolytic activity of the recombinant enzyme is completely inhibited by the serine protease inhibitor AEBSF, as previously demonstrated for the hepatopancreas collagenase.

Activity of Recombinant Collagenase Versus Peptide Substrates

The Michaelis constants of the recombinant collagenase were determined for a matched set of 15 Suc-AAP-Xaa-pNA substrates, varying only in the P1 residue. The relative balance of specificities ($k_{cat}/K_m$) of the recombinant enzyme is similar to that reported previously for the hepatopancreas enzyme versus the Arg, Lys, Gln, Leu and Phe substrates, within an error of 15–30%. The remaining 10 substrates Ala, Abu, Nva, Val, Nle, Ile, Met, Orn, Asp and Glu were selected to more fully map the specificity of crab collagenase for hydrophobic, basic and acidic residues. The substrate preference of the collagenase is quite broad. The most striking aspect of the specificity of the enzyme regards the amino acids residues it rejects. β-branched and acidic side chains are extremely poor substrates. Although the apparent binding constants ($K_m$) for Val and Ile are similar to those of the other hydrophobic substrates, $k_{cat}$ is as much as $10^3$-fold lower. Acidic residues are generally poor substrates. There is no correlation in Km for the various substrates, suggesting that there are several modes of ground state binding. This implies the existence of several distinct S1 sites or a single flexible site. A correlation for log $k_{cat}$ versus P1 residue volume ($Å^3$) is observed, irrespective of hydrophobicity. The correlation is improved and slope essentially unchanged if only the hydrophobic residues Ala, Abu, Nva, Nle, Leu, Met and Phe are included. A weaker correlation of log ($k_{cat}/K_m$) versus residue volume for this hydrophobic subset was found. These results suggest that the transition state may be stabilized in part by hydrophobic interactions. It is unclear how the enzyme binds the neutral hydrophilic and basic residues so as to minimize the effects of charge or polarity in the transition state. Bias or insensitivity in the data set may also affect the interpretation of the correlations.

Correlations of Serine Protease Specificity

The steady state kinetic parameters of chymotrypsin and elastase versus the Suc-AAP-Xaa-pNA substrate set were determined under conditions identical to those for crab collagenase. This was necessary in order to accurately compare the activities of these different enzymes. Strong positive (chymotrypsin) and negative (elastase) correlations were found for log $k_{cat}$ or log ($k_{cat}/K_m$) versus P1 residue volume (r≧0.95, eqs. 6, 8, 10 and 12, Table II). Val and Ile were omitted for chymotrypsin, while Nva and Leu were deleted for elastase, as these points deviated significantly from the rest of the data. A tight negative correlation of $K_m$ versus volume was found for chymotrypsin, but was much weaker for elastase. The sensitivity of chymotrypsin and elastase log ($k_{cat}/K_m$) to residue volume are identical and twice that of collagenase. Chymotrypsin log ($k_{cat}/K_m$) also correlated with π, the log of the octanol:water partition coefficient of the residue minus the log of the coefficient for Gly. This result with tetrapeptide amides is consistent with the correlation of log ($k_2/K_s$) for single residue esters with , where a slope of 2.2 was found. Collagenase log ($k_{cat}/K_m$) is less sensitive to π, while elastase log ($k_{cat}/K_m$) correlated well, with a slope equal and opposite that for chymotrypsin.

Contribution of the P1 Residue to Catalytic Efficiency

The relative contribution of the P1 residue to the cleavage of peptidyl substrates was estimated by comparing the catalytic efficiencies of collagenase, trypsin, chymotrypsin and elastase versus single residue and tetrapeptide P1-Arg, Phe or Ala substrates. While $k_{cat}/K_m$ of all enzymes for the peptidyl substrates are similar, within 2 to 20-fold, there is a 10 to $10^4$-fold difference in $k_{cat}/K_m$ for the single residue substrates. Trypsin derives the highest $k_{cat}/K_m$ from its single residue-Arg substrate, manifesting a 100-fold differential as compared to the peptidyl-Arg cognate. Chymotrypsin shows a 10,000-fold differential in efficiency for single residue-Phe versus peptidyl-Phe substrates, while elastase $k_{cat}/K_m$ versus single residue-Ala is 100,000-fold less than that for peptidyl-Ala. Interestingly, collagenase demonstrates identical 100,000-fold differences in $k_{cat}/K_m$ for both single residue Arg and Phe substrates, 10 to 1,000-fold greater than trypsin or chymotrypsin and similar to elastase. Collagenase and elastase show the most dependence on the P2–P4 residues for catalytic efficiency, with the low activity on single residue substrates being a consequence of small P1 residue size or non-optimal P1 residue binding.

Structurally, the degree of P2–4 binding correlates with the length of the residue 215–220 domain. This loop forms the lip of the binding pocket and forms a β sheet with the P2-Pn substrate residues. Elastase and collagenase have the longest loops, while chymotrypsin and trypsin are 1 and 2 residues shorter respectively.

EXAMPLE 2

Production of Site Directed Mutants of Collagenase

Site directed mutagenesis of collagenase was achieved in the PsFC construct described by Example 1 using the uracil laden single stranded DNA method (Kunkel, 1985). Recombinant collagenase was expressed in S. cerevisiae using the PyFC shuttle vector and purified as described in Example 1.

*Enzyme Kinetics.* Steady state kinetic assays were run in 50 mM Tris, pH 8.0, 100 mM NaCl, 20 mM $CaCl_2$, 0–2% DMF, 0–9.8% DMSO at 25° C. Benzylthioester reactions included 250 μM dithiodipyridine (Harper et al., 1981). Collagenase was active site titrated with MUTMAC (Sigma) and trypsin with MUGB (Sigma). Z-Y-Sbzl was from Enzyme Systems Products. All other substrates were from Bachem Biosciences. Spectroscopic measurements were determined as described. Initial rates were fit directly to the Michaelis Menten equation.

Collagen Cleavage Site Determination

Calf skin collagen was from US Biochemical. Collagen cleavage assays were carried out as described in Example 1, except that the microfiltration step was omitted.

Specificity for Basic Residues is Modulated by the Presence of Negative Charge in the Collagenase S1 Site Mutagenesis of collagenase to remove Asp226 from the S1 site, by substituting Gly (collagenase D226G), results in an enzyme which retains more than 50% of wild-type $k_{cat}/K_m$ versus peptidyl P1 hydrophobic substrates (Phe, Leu, Met, Ala), but maintains only 1–5% of $k_{cat}/K_m$ versus cognate positively charged substrates (Arg, Lys, Orn). Restoration of the S1 negative charge by substituting Gly189 with Asp (collagenase D226G/G189D) recovers 40–70% of wild type $k_{cat}/K_m$ versus positively charged substrates, while maintaining 15–40% of wild type $k_{cat}/K_m$, versus hydrophobic substrates. The $k_{cat}/K_m$ value towards Gln is slightly reduced for both variants. These results suggest that the collagenase S1 site possesses distinct binding determinants for hydrophobic and basic sidechains, and, unlike the trypsin S1 site, is quite tolerant of mutagenesis.

The kinetic parameters of the collagenase D226G and D226G/G189D versus shorter amide and ester substrates probed the S1 site more directly. The 20-fold $k_{cat}/K_m$ differential between collagenase D226G and wild-type for a tripeptide P1-Arg substrate is approximately the same as that for the tetrapeptide. A 100-fold differential is demonstrated with the single residue Z-K-Sbzl substrate, while efficiency versus Z-Y-Sbzl is unaffected. Consistent with the tetrapeptide amide results, collagenase D226G/G189D displays wild-type levels of $k_{cat}$ for positively charged tripeptide amide and single residue ester substrates, with a five-fold reduction in activity towards the single residue tyrosine ester. These results confirm that the observed kinetic effects are primarily manifested in the S1 site.

Collagen Specificity is Studied in the Collagenase Mutations

The collagenolytic activity of the two collagenase variants was compared directly to the wild type enzyme. Under these conditions, wild type collagenase initially attacks collagen at the ¾ cleavage site generating the characteristic ¾, ¼ fragmentation pattern. This cleavage is greater than 50% complete after 2 hours. The collagenase continues to hydrolyze the collagen such that after 16 hours essentially all full length substrate has been cleaved and secondary degradation is extensive. The ¼ length fragments are especially susceptible to further hydrolysis. Although the rate of cleavage is slowed, the general degradation pattern of the mutant collagenases is unchanged. Collagenase D226G digests collagen in a wild type progression, with a 5 to 10-fold decrease in rate, producing the ¾, ¼ cleavage pattern. The detrimental effect of the D226G mutation is somewhat less than that observed in $k_{cat}/K_m$ towards the synthetic substrates, suggesting that the extended binding sites for collagen mute the S1 deficits. Collagenase D226G/G189D manifests a 10 to 20-fold decrease in rate of collagen cleavage relative to wild type (as judged by ¾ fragment formation). A faint ¼ length triplet can be seen at 8 and 16 hours. The slower rate of collagenase D226G/G189D relative to D226G may reflect its lower activity towards hydrophobic substrates or structural perturbations caused by the mutations that were not apparent in the synthetic substrate kinetics.

Table 1 shows kinetic constants for hydrolysis of Suc-AAP-Xaa-pNA by wild-type crab collagenase (FC) and mutants. Reaction conditions were 50 mM Tris, 100 mM NaCl, 20 mM CaCl$_2$, 1% DMF (or 2% DMSO, Suc-AAP-Gln-pNA), pH 8.0 at 25° C. Each represent the means of two determinations. Each determination included the observed hydrolysis rates for reactions at five concentrations of substrate. The standard deviations were less than 10% in all cases.

TABLE 1

| Substrate/Enzyme (Suc-AAP-Xaa-pNA) | $k_{cat}$ (/min) | $K_m$ (μM) | $k_{cat}/K_m$ (μM/min) |
|---|---|---|---|
| Arginine | | | |
| FC WT | 1500 | 18 | 80 |
| FC D226G | 1400 | 480 | 2.9 |
| FC D226G/G189D | 2600 | 46 | 55 |
| Lysine | | | |
| FC WT | 190 | 53 | 3.6 |
| FC D226G | 28 | 1100 | 0.024 |
| FC D226G/G189D | 310 | 230 | 1.4 |
| Ornithine | | | |
| FC WT | 340 | 720 | 0.47 |
| FC D226G | 14 | 630 | 0.023 |
| FC D226G/G189D | — | — | 0.288 |
| Phenylalanine | | | |
| FC WT | 2900 | 310 | 9.5 |
| FC D226G | 2350 | 340 | 6.9 |
| FC D226G/G189D | 800 | 580 | 1.4 |
| Leucine | | | |
| FC WT | 1700 | 190 | 9.1 |
| FC D226G | 1300 | 270 | 4.8 |
| FC D226G/G189D | 1250 | 400 | 3.1 |
| Methionine | | | |
| FC WT | 1500 | 360 | 4.2 |
| FC D226G | 1100 | 380 | 2.9 |
| FC D226G/G189D | 770 | 540 | 1.4 |
| Alanine | | | |
| FC WT | 110 | 820 | 0.13 |
| FC D226G | 86 | 1100 | 0.019 |
| FC D226G/G189D | 70 | 1300 | 0.052 |
| Glutamine | | | |
| FC WT | 2000 | 1800 | 1.1 |
| FC D226G | — | — | 0.33 |
| FC D226G/G189D | — | — | 0.33 |

Table 2 shows kinetic constants for hydrolysis of amide and ester substrates by wild-type crab collagenase and mutants. The substrate was (Suc-AAP-Xaa-pNA)

Reaction conditions were 50 mM Tris, 100 mM NaCl, 20 mM CaCl$_2$, 1% DMF (or 9.8% DMSO, Z-Tyr-Sbzl), pH 8.0 at 25° C. Each determination included the observed hydrolysis rates for reactions at five concentrations of substrate. The standard deviations were less than 10% in all cases.

TABLE 2

| Substrate/Enzyme | $k_{cat}$ (/min) | $K_m$ (μM) | $k_{cat}/K_m$ (μM/min) |
|---|---|---|---|
| Z-GPR-pNA | | | |
| FC WT | 93 | 230 | 0.43 |
| FC D226G | 2.2 | 100 | 0.022 |
| FC D226G/G189D | 220 | 250 | 0.87 |
| Z-K-Sbzl | | | |
| FC WT | 460 | 100 | 4.5 |
| FC D226G | 9.1 | 190 | 0.048 |
| FC D226G/G189D | 1400 | 150 | 9.5 |
| Z-Y-Sbzl | | | |
| FC WT | 2700 | 41 | 64 |
| FC D226G | 2600 | 49 | 53 |
| FC D226G/G189D | 625 | 52 | 12 |

Further Variant Preparations

In this description the residue numbers correspond to linear numbering (rather than the frequently and previously used chymotrypsinogen numbering system). In the following linear numbering system some key residue numbering shifts are where previously described histidine 57 is now histidine 41, serine 195 is now serine 178, aspartic acid 102 is now 87, aspartic acid 226 is 206 and aspartic acid 60 is 44, while glycine 189 is 172. Parenthesis will be used to denote the numbers for some other residues mentioned below in the linear numbering system. Both numbering systems are known and used by persons skilled in the art.

In addition to the S1 site, at least one additional enzyme subsite possesses strong sequence preference. By using a nucleophillic acyl transfer protocol, in which mixtures of peptides compete with water and with each other for attack on the acyl enzyme, a significiant preference of 10–100 fold was found in favor of Arg and Lys at position P1'. Hydrophobic side chains are also favored at this site, although to a lesser degree. From our analysis of the collagenase-ecotin crystal structure, the S1' site forms a shallow cavity arising from the juxtaposition of two surface loops at residues 41–46 (57–62) and 19–26 (34–42). The Cys26(42)-Cys42 (58) disulfide bond and the aromatic side chain of Tyr24(40) form the two sides of the cavity and make van der Waals interactions with the P1'-met85 of ecotin. These surfaces provide a rationale for the hydrophobic amino acid preference at this position. Modelling of Arg and Lys side-chains at this position shows that charged hydrogen bonds could be formed by the terminal amine or guanidinium group with the backbone carbonyl oxygen atoms of His41(57) and Cys42 (58). Additionally, it appears possible that surface side chain of Asp44(60), could be oriented to interact electrostatically with a P'1 basic residue of the substrate. Thus, mutagenesis of Asp44 to Gly could significantly reduce the preference of the S1' site for basic P1' residues.

Alternatively, acidic P1' specificity may be conferred by replacing Asp44 with Arg or Lys. The combined engineering of the collagenase S1 and S1' sites, which straddle the cleaved bond of the peptide substrate, may generate variant proteases of exceptionally high specificity.

EXAMPLE 3

Procollagenase was expressed in an insoluble form in *E. coli* using an alkaline phosphatase promoter with an STII signal peptide. The naturally occurring signal peptide of preprocollagenase was replaced with the STII signal peptide and the resulting DNA construct was placed under transcriptional control with the alkaline phosphatase promoter. A six histidine tag was inserted between the signal sequence and the pro sequences to aid in purification of the enzyme. By producing the enzyme in insoluble inclusion bodies in the bacteria, the protein could be readily isolated from the majority of the bacterial proteins by sonication followed by differential centrifugation. The partially purified inclusion bodies were solubilized with 6M urea and the histidine tagged procollagenase was then purified on a Nickel column which selectively bound the six histidines attached to procollagenase. By washing the column with buffer containing no urea the collagenase refolded on the column. The refolded enzyme was then eluted from the columns. It could be activated with catalytic amounts of trypsin which yielded mature, active collagenase.

Specifically, after 20 hours of growth in the low phosphate induction medium, the cells were pelleted. The pellet was then resuspended in ice cold water and sonicated. After centrifugation the pellet, which contained the insoluble enzyme, was solubilized in 6M Urea, 50 mM Tris pH 8, 500 mM NaCl and 20 mM CaCl2. This slurry was spun in a centrifuge to remove any insoluble material. The supernatant was directly loaded onto a Ni2+-NTA column resin (Qiagen). The column was washed with 50 mL of 6M Urea, 50 mM Tris pH8, 1M NaCl and 20 mm CaCl2. A 500 mL reverse Urea gradient (6M-0M) was then run over a period of 12 hours to refold the enzyme immobilized on the column. The enzyme was then eluted with an imidazole gradient (0–600 mM) and activated with agarose bound trypsin to remove the N-terminal pro-peptide and the 6xHis tag. Activation was monitored by an activity assay using the substrate suc-AAPL-PNA. This expression, refolding and purification system provides rapid production of homogeneous, pure collagenase for enzymatic analysis of both wild type and variant forms of the enzyme.

EXAMPLE 4

To eliminate the need for zymogen activation, the gene can be modified to direct the secretion of mature collagenase in yeast. Thus, the first codon of mature collagenase, coding for Ile, is abutted to the prepeptide of yeast alpha factor. This is done by deleting the sequences that encode the "PRO" sequence of procollagenase so as to produce a construct with the alpha factor leader sequence directly in frame with the mature collagenase. Secretion of the precollagenase from yeast results in removal of the presequence and release of mature collagenase into the media of the yeast culture.

EXAMPLE 5

Insect cells and the lytic baculovirus, Autographa californica nuclear polyhedrosis virus (AcNPV), have been used to express the collagenase zymogen gene with and without the 6xHis tag (N-term). Transfer vector constructs were made that put the collagenase gene under the strong baculovirus polyhedrin promoter and utilized the secretion signal sequence from glycoprotein gp67, one of the most efficient AcNPV-encoded signal sequences for protein secretion. The polyhedrin based transfer vector allows for double recombination between the flanking regions of the polyhedrin gene when co-transfected with linearized baculorirus genome DNA (BaculoGold DNA from PharMingen) in Sf9 insect cells. The Sf9 insect cell line is derived from the pupal ovarian tissue of the fall army worm, Spodoptera frugiperda. The polyhedrin gene is non-essential for viral replication and infection in tissue culture and disruption of this gene gives an occlusion body-negative phenotype. Wild-type baculovirus background is very low due to a lethal deletion in the linearized genome DNA which is rescued by recombination with the transfer vector. A single recombinant baculovirus was obtained by plaque purification and subsequently amplified using Sf9 cells. Trial expression using the High Five cell line from the cabbage looper, *Trichoplusia ni*, showed high levels of collagenase production ranging from 10 to 100 milligrams per liter.

It is to be understood that while the invention has been described above in conjunction with preferred specific embodiments, the description and examples are intended to illustrate and not limit the scope of the invention, which is defined by the scope of the appended claims.

It is claimed:

1. An isolated procollagenase having an amino acid sequence of SEQ ID NO: 5.

2. The procollagenase of claim 1 wherein glycine substitutes for aspartic acid at position 235 of SEQ ID NO: 5.

3. The procollagenase of claim 1 wherein aspartic acid substitutes for glycine at position 201 and glycine substitutes for aspartic acid at position 235 of SEQ ID NO: 5.

4. A storage-stabilized composition, useful for collagen degradation, comprising:

a procollagenase of Seq ID NO 5; and an acidic agent.

5. The composition as in claim 4 wherein the acidic agent is sufficient to maintain a pH of about 4 or less.

6. The composition as in claim 4 wherein the procollagenase is in active form when the acidic agent is neutralized, the active form being capable of degrading collagen.

7. The composition as in claim 6 wherein formation of the active form is sped by admixing the procollagenase with a protease capable of selectively cleaving the propeptide of Seq ID NO 6 from said procollagenase.

8. The composition as in claim 4 further comprising a neutralizing component sufficient to neutralize the acidic agent, the neutralizing component being maintained separate from the acidic agent until neutralization is desired.

9. The composition as in claim 8 wherein the neutralizing component further includes a protease capable of selectively cleaving the propeptide of Seq ID NO 6 from said procollagenase.

10. The composition as in claim 4 wherein glycine substitutes for aspartic acid at position 235 of Seq ID NO 5.

11. The composition as in claim 10 wherein aspartic acid substitutes for glycine at position 201 of Seq ID NO 5.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 734 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
ATTGTGGGTG GCGTTGAGGC AGTGCCCAAC TCGTGGCCCC ACCAGGCAGC TCTCTTCATT      60
GACGACATGT ACTTCTGCGG TGGCTCCCTC ATATCCCTG AGTGGATCCT GACTGCTGCT      120
CACTGCATGG ATGGGGCCGG TTTTGTGGAT GTGGTTCTGG GGCTCACAA TATTCGTGAG       180
GACGAAGCCA CACAGGTAAC CATACAGAGC ACCGACTTCA CGGTCCACGA GAACTATAAC      240
TCTTTCGTCA TATCGAATGA TATCGCCGTC ATCAGGCTGC CTTCACCAGT AACCCTGACT      300
GCGGCAATTG CTACCGTTGG TCTGCCTTCA ACTGATGTCG GTGTTGGAAC GGTAGTAACT      360
CCAACTGGCT GGGGCCTACC ATCAGACTCT GCCCTTGGGA TTTCTGACGT TCTTCGCCAA      420
GTGGATGTCC CCATCATGAG TAATGCAGAC TGTGACGCAG CTACGGCAT TGTGACAGAT       480
GGAAATATCT GCATTGACTC AACTGGTGGC AAGGGTACTT GTAACGGTGA CTCAGGTGGC      540
CCTCTCAACT ATAACGGACT GACCTATGGC ATCACTTCCT TCGGTGCGGC GGCTGGTTGT      600
GAGGCTGGCT ACCCAGATGC CTTCACTCGC GTCACTTATT CCTGGACTG GATCCAGACA      660
CAGACGGGCA TCACTCCATA AGCGACAAGG ACAAGATACG ACTGATGGGA GCCCAAAGA       720
TTGTATATGT GTCT                                                       734
```

( 2 ) INFORMATION FOR SEQ ID NO:2:

( i ) SEQUENCE CHARACTERISTICS:
        ( A ) LENGTH: 821 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

```
AGCGGCAACC CCGCGGCTGG CACAGAATGG CGTTGGAAGT CTCCGAAGCC ACTTATGACA      60
CCCATTGGCC CTGTAAAGTC ATCCCGCATT GTGGGTGGCG TTGAGGCAGT GCCCAACTCG      120
TGGCCCCACC AGGCAGCTCT CTTCATTGAC GACATGTACT TCTGCGGTGG CTCCCTCATA      180
TCCCCTGAGT GGATCCTGAC TGCTGCTCAC TGCATGGATG GGGCCGGTTT TGTGGATGTG      240
GTTCTGGGGG CTCACAATAT TCGTGAGGAC GAAGCCACAC AGGTAACCAT ACAGAGCACC      300
GACTTCACGG TCCACGAGAA CTATAACTCT TTCGTCATAT CGAATGATAT CGCCGTCATC      360
AGGCTGCCTT CACCAGTAAC CCTGACTGCG GCAATTGCTA CCGTTGGTCT GCCTTCAACT      420
GATGTCGGTG TTGGAACGGT AGTAACTCCA ACTGGCTGGG GCCTACCATC AGACTCTGCC      480
CTTGGGATTT CTGACGTTCT TCGCCAAGTG GATGTCCCCA TCATGAGTAA TGCAGACTGT      540
GACGCAGTCT ACGGCATTGT GACAGATGGA AATATCTGCA TTGACTCAAC TGGTGGCAAG      600
GGTACTTGTA ACGGTGACTC AGGTGGCCCT CTCAACTATA ACGGACTGAC CTATGGCATC      660
```

```
ACTTCCTTCG GTGCGGCGGC TGGTTGTGAG GCTGGCTACC CAGATGCCTT CACTCGCGTC      720

ACTTATTTCC TGGACTGGAT CCAGACACAG ACGGGCATCA CTCCATAAGC GACAAGGACA      780

AGATACGACT GATGGGAGCC CCAAAGATTG TATATGTGTC T                         821
```

( 2 ) INFORMATION FOR SEQ ID NO:3:

( i ) SEQUENCE CHARACTERISTICS:
        ( A ) LENGTH: 866 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

```
ATGATCGTCA AGCTTGCTCT CATCCTCGTC TGCGTCGCCC TAGCTAGCGG CAACCCCGCG       60

GCTGGCACAG AATGGCGTTG GAAGTCTCCG AAGCCACTTA TGACACCCAT GGCCCTGTA       120

AAGTCATCCC GCATTGTGGG TGGCGTTGAG GCAGTGCCCA ACTCGTGGCC CACCAGGCA       180

GCTCTCTTCA TTGACGACAT GTACTTCTGC GGTGGCTCCC TCATATCCCC TGAGTGGATC      240

CTGACTGCTG CTCACTGCAT GGATGGGGCC GGTTTTGTGG ATGTGGTTCT GGGGGCTCAC      300

AATATTCGTG AGGACGAAGC CACACAGGTA ACCATACAGA GCACCGACTT CACGGTCCAC      360

GAGAACTATA ACTCTTTCGT CATATCGAAT GATATCGCCG TCATCAGGCT GCCTTCACCA      420

GTAACCCTGA CTGCGGCAAT TGCTACCGTT GGTCTGCCTT CAACTGATGT CGGTGTTGGA      480

ACGGTAGTAA CTCCAACTGG CTGGGGCCTA CCATCAGACT CTGCCCTTGG GATTTCTGAC      540

GTTCTTCGCC AAGTGGATGT CCCCATCATG AGTAATGCAG ACTGTGACGC AGTCTACGGC      600

ATTGTGACAG ATGGAAATAT CTGCATTGAC TCAACTGGTG GCAAGGGTAC TTGTAACGGT      660

GACTCAGGTG GCCCTCTCAA CTATAACGGA CTGACCTATG GCATCACTTC CTTCGGTGCG      720

GCGGCTGGTT GTGAGGCTGG CTACCCAGAT GCCTTCACTC GCGTCACTTA TTTCCTGGAC      780

TGGATCCAGA CACAGACGGG CATCACTCCA TAAGCGACAA GGACAAGATA CGACTGATGG      840

GAGCCCCAAA GATTGTATAT GTGTCT                                          866
```

( 2 ) INFORMATION FOR SEQ ID NO:4:

( i ) SEQUENCE CHARACTERISTICS:
        ( A ) LENGTH: 226 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:4:

```
Ile Val Gly Gly Val Glu Ala Val Pro Asn Ser Trp Pro His Gln Ala
 1               5                  10                  15

Ala Leu Phe Ile Asp Asp Met Tyr Phe Cys Gly Gly Ser Leu Ile Ser
            20                  25                  30

Pro Glu Trp Ile Leu Thr Ala Ala His Cys Met Asp Gly Ala Gly Phe
        35                  40                  45

Val Asp Val Val Leu Gly Ala His Asn Ile Arg Glu Asp Glu Ala Thr
    50                  55                  60

Gln Val Thr Ile Gln Ser Thr Asp Phe Thr Val His Glu Asn Tyr Asn
65                  70                  75                  80
```

```
Ser  Phe  Val  Ile  Ser  Asn  Asp  Ile  Ala  Val  Ile  Arg  Leu  Pro  Ser  Pro
               85                       90                       95

Val  Thr  Leu  Thr  Ala  Ala  Ile  Ala  Thr  Val  Gly  Leu  Pro  Ser  Thr  Asp
              100                      105                      110

Val  Gly  Val  Gly  Thr  Val  Val  Thr  Pro  Thr  Gly  Trp  Gly  Leu  Pro  Ser
              115                      120                      125

Asp  Ser  Ala  Leu  Gly  Ile  Ser  Asp  Val  Leu  Arg  Gln  Val  Asp  Val  Pro
          130                      135                      140

Ile  Met  Ser  Asn  Ala  Asp  Cys  Asp  Ala  Val  Tyr  Gly  Ile  Val  Thr  Asp
145                      150                      155                      160

Gly  Asn  Ile  Cys  Ile  Asp  Ser  Thr  Gly  Gly  Lys  Gly  Thr  Cys  Asn  Gly
              165                      170                      175

Asp  Ser  Gly  Gly  Pro  Leu  Asn  Tyr  Asn  Gly  Leu  Thr  Tyr  Gly  Ile  Thr
              180                      185                      190

Ser  Phe  Gly  Ala  Ala  Ala  Gly  Cys  Glu  Ala  Gly  Tyr  Pro  Asp  Ala  Phe
              195                      200                      205

Thr  Arg  Val  Thr  Tyr  Phe  Leu  Asp  Trp  Ile  Gln  Thr  Gln  Thr  Gly  Ile
          210                      215                      220

Thr  Pro
225
```

( 2 ) INFORMATION FOR SEQ ID NO:5:

( i ) SEQUENCE CHARACTERISTICS:
        ( A ) LENGTH: 255 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:5:

```
Ser  Gly  Asn  Pro  Ala  Ala  Gly  Thr  Glu  Trp  Arg  Trp  Lys  Ser  Pro  Lys
1                   5                        10                       15

Pro  Leu  Met  Thr  Pro  Ile  Gly  Pro  Val  Lys  Ser  Ser  Arg  Ile  Val  Gly
               20                       25                       30

Gly  Val  Glu  Ala  Val  Pro  Asn  Ser  Trp  Pro  His  Gln  Ala  Ala  Leu  Phe
               35                       40                       45

Ile  Asp  Asp  Met  Tyr  Phe  Cys  Gly  Gly  Ser  Leu  Ile  Ser  Pro  Glu  Trp
          50                       55                       60

Ile  Leu  Thr  Ala  Ala  His  Cys  Met  Asp  Gly  Ala  Gly  Phe  Val  Asp  Val
65                       70                       75                       80

Val  Leu  Gly  Ala  His  Asn  Ile  Arg  Glu  Asp  Glu  Ala  Thr  Gln  Val  Thr
               85                       90                       95

Ile  Gln  Ser  Thr  Asp  Phe  Thr  Val  His  Glu  Asn  Tyr  Asn  Ser  Phe  Val
              100                      105                      110

Ile  Ser  Asn  Asp  Ile  Ala  Val  Ile  Arg  Leu  Pro  Ser  Pro  Val  Thr  Leu
              115                      120                      125

Thr  Ala  Ala  Ile  Ala  Thr  Val  Gly  Leu  Pro  Ser  Thr  Asp  Val  Gly  Val
              130                      135                      140

Gly  Thr  Val  Val  Thr  Pro  Thr  Gly  Trp  Gly  Leu  Pro  Ser  Asp  Ser  Ala
145                      150                      155                      160

Leu  Gly  Ile  Ser  Asp  Val  Leu  Arg  Gln  Val  Asp  Val  Pro  Ile  Met  Ser
              165                      170                      175

Asn  Ala  Asp  Cys  Asp  Ala  Val  Tyr  Gly  Ile  Val  Thr  Asp  Gly  Asn  Ile
              180                      185                      190
```

```
Cys  Ile  Asp  Ser  Thr  Gly  Gly  Lys  Gly  Thr  Cys  Asn  Gly  Asp  Ser  Gly
          195                      200                      205

Gly  Pro  Leu  Asn  Tyr  Asn  Gly  Leu  Thr  Tyr  Gly  Ile  Thr  Ser  Phe  Gly
     210                      215                      220

Ala  Ala  Ala  Gly  Cys  Glu  Ala  Gly  Tyr  Pro  Asp  Ala  Phe  Thr  Arg  Val
225                      230                      235                       240

Thr  Tyr  Phe  Leu  Asp  Trp  Ile  Gln  Thr  Gln  Thr  Gly  Ile  Thr  Pro
               245                      250                      255
```

( 2 ) INFORMATION FOR SEQ ID NO:6:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:6:

```
Ser  Gly  Asn  Pro  Ala  Ala  Gly  Thr  Glu  Trp  Arg  Trp  Lys  Ser  Pro  Lys
1                   5                   10                      15

Pro  Leu  Met  Thr  Pro  Ile  Gly  Pro  Val  Lys  Ser  Ser  Arg
               20                  25
```